United States Patent
Andersen

(10) Patent No.: US 10,034,108 B2
(45) Date of Patent: Jul. 24, 2018

(54) METHOD FOR THE FITTING OF A HEARING AID, A SYSTEM FOR FITTING A HEARING AID AND A HEARING AID

(75) Inventor: Svend Vitting Andersen, Espergarde (DK)

(73) Assignee: WIDEX A/S, Lynge (DK)

( * ) Notice: Subject to any disclaimer, the term of this patent is extended or adjusted under 35 U.S.C. 154(b) by 1008 days.

(21) Appl. No.: 12/238,790

(22) Filed: Sep. 26, 2008

(65) Prior Publication Data
US 2009/0028351 A1    Jan. 29, 2009

Related U.S. Application Data

(63) Continuation-in-part of application No. PCT/DK2006/000535, filed on Sep. 29, 2006.

(30) Foreign Application Priority Data

Mar. 31, 2006 (DK) ................................. 2006 00463

(51) Int. Cl.
*H04R 29/00* (2006.01)
*H04R 25/00* (2006.01)
*A61B 5/12* (2006.01)

(52) U.S. Cl.
CPC ............ *H04R 25/70* (2013.01); *A61B 5/123* (2013.01); *H04R 25/30* (2013.01); *H04R 25/305* (2013.01); *H04R 2225/43* (2013.01)

(58) Field of Classification Search
CPC .... H04R 25/70; H04R 25/30; H04R 2225/43; H04R 25/305; H04R 2225/49; A61B 5/123; G10L 21/02

(Continued)

(56) References Cited

U.S. PATENT DOCUMENTS

| 4,548,082 A | 10/1985 | Engebretson et al. |
| 4,989,251 A | 1/1991 | Mangold |

(Continued)

FOREIGN PATENT DOCUMENTS

| DE | 10064210 A1 | 7/2002 |
| DE | 100264210 A1 | 7/2002 |

(Continued)

OTHER PUBLICATIONS

Martin et al., "Adaptive Dynamic Range Optimisation for Hearing Aids", Acoustics Australia, 2001. vol. 1, No. 1, pp. 21-24.*

(Continued)

*Primary Examiner* — Vivian Chin
*Assistant Examiner* — Con P Tran
(74) *Attorney, Agent, or Firm* — Sughrue Mion, PLLC

(57) ABSTRACT

A method for use in the fitting of a hearing aid comprises the steps of providing a sound recording of a user environment, feeding the sound recording to the hearing aid as a sound input signal (8a), processing the sound input signal according to a scheme defined by preselected settings of a number of parameters so as to provide a processed signal (8b), adjusting the setting of at least one parameter, performing a statistical analysis of the magnitude of the processed signal or of the input signal in at least one frequency band, which statistical analysis is reset when a parameter is adjusted during the fitting, and displaying a graphical representation (10, 11) of the results of said statistical analysis. The invention also provides a system for fitting a hearing aid and a hearing aid.

18 Claims, 5 Drawing Sheets

(58) Field of Classification Search
USPC .......... 381/60, 104, 58, 321, 323, 122, 317, 381/94.1, 314; 600/559; 73/385, 584; 704/E21.002
See application file for complete search history.

(56) References Cited

U.S. PATENT DOCUMENTS

| | | | |
|---|---|---|---|
| 5,303,306 A * | 4/1994 | Brillhart et al. | 381/315 |
| 5,687,241 A * | 11/1997 | Ludvigsen | 381/312 |
| 5,729,658 A * | 3/1998 | Hou et al. | 704/270 |
| 6,731,767 B1 * | 5/2004 | Blamey et al. | 381/312 |
| 7,599,507 B2 | 10/2009 | Hansen | |
| 2004/0190739 A1 * | 9/2004 | Bachler et al. | 381/314 |
| 2008/0123883 A1 * | 5/2008 | Blamey et al. | 381/312 |

FOREIGN PATENT DOCUMENTS

| | | |
|---|---|---|
| EP | 0 732 036 B1 * | 5/1997 |
| EP | 1404152 A2 | 3/2004 |
| JP | 59063899 A | 4/1984 |
| JP | 5115096 A | 5/1993 |
| JP | 2005537702 A | 12/2005 |
| WO | 01/54456 A1 | 7/2001 |
| WO | 02054456 A2 | 7/2002 |
| WO | 2005018725 A2 | 2/2005 |

OTHER PUBLICATIONS

Kuk et al., "Using Digital Hearing Aids to Visualize Real-Life Effects of Signal Processing", The Hearing Journal, Apr. 2004. vol. 57, No. 4, pp. 40, 42, 44, 46, 48-49.*

Kuk et al., "Hearing Aid Fitting and the Use of Simulated Sound Environments", The Hearing Review, Aug. 2004.*

Office Action for JP2009-501851 dated May 31, 2011 with English Translation.

* cited by examiner

METHOD FOR THE FITTING OF A HEARING AID, A SYSTEM FOR FITTING A HEARING AID AND A HEARING AID

RELATED APPLICATIONS

The present application is a continuation-in-part of application no. PCT/DK2006000535 filed on Sep. 29, 2006 and published as WO-A1-2007112737, the contents of which are incorporated herein by reference. The present application is based on and claims priority from PA200600463 filed on Mar. 31, 2006, the contents of which are incorporated herein by reference.

BACKGROUND OF THE INVENTION

1. Field of the Invention

The present invention relates to the field of hearing aids. The invention, more specifically, relates to a method for the fitting of a hearing aid, to a system for fitting a hearing aid and to a hearing aid.

2. Description of the Related Art

U.S. Pat. No. 4,548,082 provides a hearing aid and a host computer for supplying sets of signals to the hearing aid in a total system. The host computer controls the emission of stored sounds by a loudspeaker. The host computer displays hearing threshold, most comfortable loudness level, uncomfortable loudness level, and performance characteristics of the hearing aid (e.g. mapping conversational speech onto the auditory area). The operator may enter adjusted values of gains, and the host computer computes how the hearing aid would, if programmed with the adjusted values, reposition the conversational speech spectrum on the stationary auditory area. The informational display shows the auditory area with the repositioned conversational speech spectrum (hearing aid response curves). Adjusted and unadjusted values of various of limits and gains are also output for operator reference.

DE-B4-10064210 provides a system for the testing of a hearing aid, wherein a fitting computer can read out and display input levels and output levels of sound in respective frequency bands.

It is nowadays a standard practice to fit hearing aids in an interactive session, the hearing aid user wearing a hearing aid, while a fitter remotely programs it and plays back sound to the user in order to provide him or her with an immediate acoustic impression of the performance of the hearing aid. The user comments to the fitter about his or her perceptions and about any perceived problems, and the fitter may then suggest adaptations and fine tunings of the settings and may program them into the hearing aid and again play back sound samples for letting the user try the adapted settings.

Traditionally hearing aids have been fitted to the hearing loss of the user using playbacks of standardized recordings of sound. These recordings reflect typical sound environments, such as street noise, party noise, dialogue, etc. Using these recordings the user can try out different settings and comment to the fitter, who can then adapt the parameters according to which the hearing aid modifies input sounds, so as to provide the best possible compensation for the hearing loss of the user, in various situations.

Advanced hearing aids may include several programs or schemes among which the user can choose depending on the current sound environment or listening situation, each of these programs being defined by a set of parameters, which can be programmed and tuned by the fitter. Parameters programmable for respective schemes are amplification in specific frequency bands, weighting of signals from different input transducers in order to provide various degrees of directionality, feedback suppression, adaptive noise reduction etc.

As the long-term statistical distributions of the pre-recorded samples of loud and soft signals are known, static curves illustrating the distributions are typically preprogrammed for ready presentation to the fitter during the fitting session. This presentation may simply be of the statistical distribution of the input signal itself, or the presentation may be of the statistical distribution of the output signal, which would be produced by the hearing aid based on the input signal and the current settings of the hearing aid. The presentation of the statistical distribution allows the fitter to assess and consider signals for judging what the hearing aid should do and for guidance in the event further adaptation might be requested.

There is however a desire from the users of hearing aids to have the fitting performed on actual sound recordings from the environments in which they find themselves, e.g. actual recordings from their workplace or other places of interest to the user. Such recordings are commonly referred to as "life sounds". By fitting the hearing aid to the user using sounds from the actual environment, the performance of the hearing aid may be better adapted to those particular environments that are important to the user, as compared to a fitting using standardized sounds.

However, the use of life sounds, which are not standardized, presents the fitter with new problems when fitting the hearing aid.

One such problem is that the statistical distribution of the "life sounds" is unlikely to match any of the pre-programmed statistical distributions, so that these cannot be used. Moreover, as there is an infinite number of life sounds with different distributions, it is almost impossible for the fitter to gain any experience as to how the distribution is in any specific type of signal, and how it would be represented on the display during fitting.

Another problem stems from the fact that modem hearing aids include automated functions, i.e. functions that are activated by the hearing aid itself, such as adaptive directionality, adaptive feedback suppression, adaptive noise reduction, speech enhancement, variable signal gain or compression, etc. With sounds other than the standardized sounds it is not obvious to the fitter how the automated adaptive functions influence the final output, i.e. to the fitter there is a loss of transparency in what the hearing aid does to the input signals.

A further problem in relation to the transparency of the automated adaptive functions, in particular in the noise reduction or speech enhancement systems, is that a transient or short-term change of the spectral distribution may cause changes in the way those systems operate. In particular a change in the spectral distribution may alter the masking relations between the sounds, i.e. the fact that a sound with a given frequency and a high sound level, makes inaudible sounds at frequencies close to that frequency but having lower sound levels.

SUMMARY OF THE INVENTION

It is the object to overcome the above problem with the transparency, in particular when fitting a hearing aid using life sounds.

The invention, in a first aspect, provides a method for the fitting of a hearing aid, comprising the steps of providing a sound recording of a user environment, feeding the sound recording to the hearing aid as an input signal, modifying the input signal according to a scheme defined by preselected settings of a number of parameters so as to provide a modified signal, performing a statistical analysis of the magnitude of at least one of the modified signal and the input signal in at least one frequency band, displaying a graphical representation of the results of the statistical analysis, adjusting the setting of at least one of said parameters, and restarting the statistical analysis.

By performing the statistical analysis, and presenting the results thereof to the fitter as a graphical representation, the fitter is allowed to assess and consider the actual sound signal, in turn putting him in a better position for judging what the hearing aid does by its automatic facilities. It thus becomes possible to fit the hearing aid better to the actual sound environments in which the user finds himself in his daily life. By restarting the statistical analysis it is prevented that old data, representing the signal output resulting from older settings, could falsify the statistical analysis, and could mask the information presented to the fitter.

The invention, in a second aspect, provides a system for fitting a hearing aid, the hearing aid having means for receiving an input signal representing a sequence of sounds recorded in a user environment, and means for modifying said input signal according to a scheme defined by preselected parameters so as to provide a modified signal, the system comprising means for adjusting at least one of said parameters, means for performing a statistical analysis on the magnitude a least one of the modified signal and the input signal in at least one frequency band, which statistical analysis is reset in the event a parameter is adjusted during the fitting, and means for displaying a graphic representation of the results of the statistical analysis.

The invention, in a third aspect, provides a hearing aid having means for receiving a signal representing a sequence of sounds recorded in a user environment, means for processing said signal according to a scheme defined by preselected parameters so as to provide a processed signal, means for adjusting at least one of said parameters, means for performing a statistical analysis on a least one of the magnitude of the processed signal and the input signal in at least one frequency band, which statistical analysis is reset when a parameter is adjusted during the fitting, and means for communicating the results of said statistical analysis to a display means for the display of a graphic representation of the results of the statistical analysis.

According to a first preferred embodiment, the results of said statistical analysis are displayed as an upper and lower magnitude limit for said at least one frequency band. This is convenient for the fitter, as these results may then be presented as further information in an otherwise conventional representation relating to the hearing aid.

According to a preferred embodiment, the statistical analysis is performed continuously based on said modified signal, and said display of the result is continuously updated accordingly. This allows the fitter to follow the development of the statistical analysis over time towards a more or less steady state representing the long term statistics for the specific sound environments used during the fitting.

According to a further preferred embodiment, the statistical analysis is based on a percentile estimator, and said upper and lower magnitude limits are based on respective upper and lower percentiles. A percentile estimator is comparatively easy to implement, be it in the fitting software or in the hearing aid, yet is yields results useful to the fitter. Some existing hearing aids already have a built-in percentile estimator, which can then be used, provided that the hearing aid is modified, e.g. suitably reprogrammed, so that it can communicate the results, or parameters corresponding to the results, of the statistical analysis back to the computer.

According to yet a further embodiment, the upper percentile is the 90% percentile. Experience has shown that this value yields useful results for the fitter. Likewise it has been found that a useful value for the lower percentile is the 10% percentile.

According to a further preferred embodiment of the method according to the invention, the statistical analysis is performed for a number of frequency bands, and the upper and lower magnitude limits are displayed as continuous curves as a function of the frequency. Making the analysis with a high frequency-resolution and displaying continuous curves facilitates the recognition of those curves, by the fitter.

According to another preferred embodiment, the statistical analysis is performed using a short-term Fourier transform. The use of a fast Fourier transform is easy to implement and allows different ways of displaying the statistical information to the fitter as compared to the percentile estimators.

According to yet another preferred embodiment the statistical analysis is performed in the hearing aid. This is in particular of advantage if the hearing aid is of a type already incorporating a percentile estimator.

Alternatively, the statistical analysis is performed in a fitting computer connected to the hearing aid during fitting. This may be necessary if the hearing aid does not incorporate the facilities to provide the desired statistical results, e.g. if the fitter wishes to use a fast Fourier transform rather than a built-in percentile estimator facility.

Moreover, according to a different preferred embodiment both the modifying of said signal according to a desired scheme, and the performing of the statistical analysis on the magnitude of the modified signal are performed in a fitting computer using a computer model of the hearing aid. This may allow the fitter to simulate the fitting of a hearing aid, without having the actual hearing aid present.

BRIEF DESCRIPTION OF THE DRAWINGS

By way of example, there is shown and described a preferred embodiment of this invention. As will be realized, the invention is capable of other different embodiments, and its several details are capable of modification in various, obvious aspects all without departing from the invention. Accordingly, the drawings and descriptions will be regarded as illustrative in nature and not as restrictive. In the drawings.

DETAILED DESCRIPTION

Figure 1:
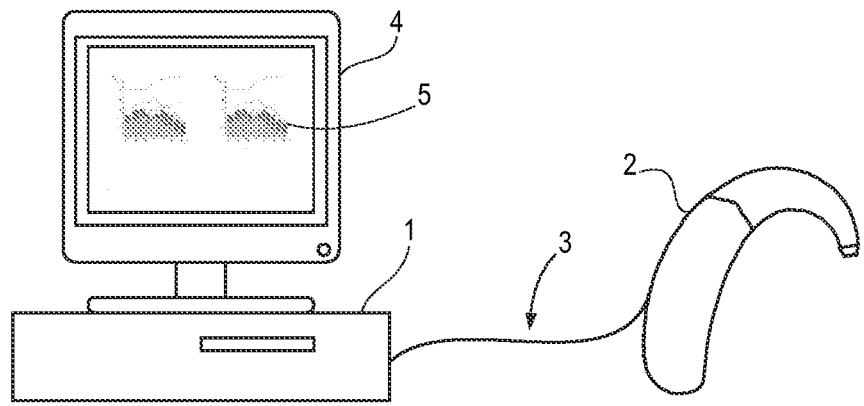
FIG. 1 illustrates a system used during the fitting of a hearing aid.

Referring first to FIG. 1, there is shown a system according to the invention. The system comprises a computer with display 4, a cable connection 3 and a hearing aid 2. 1

Figure 2:
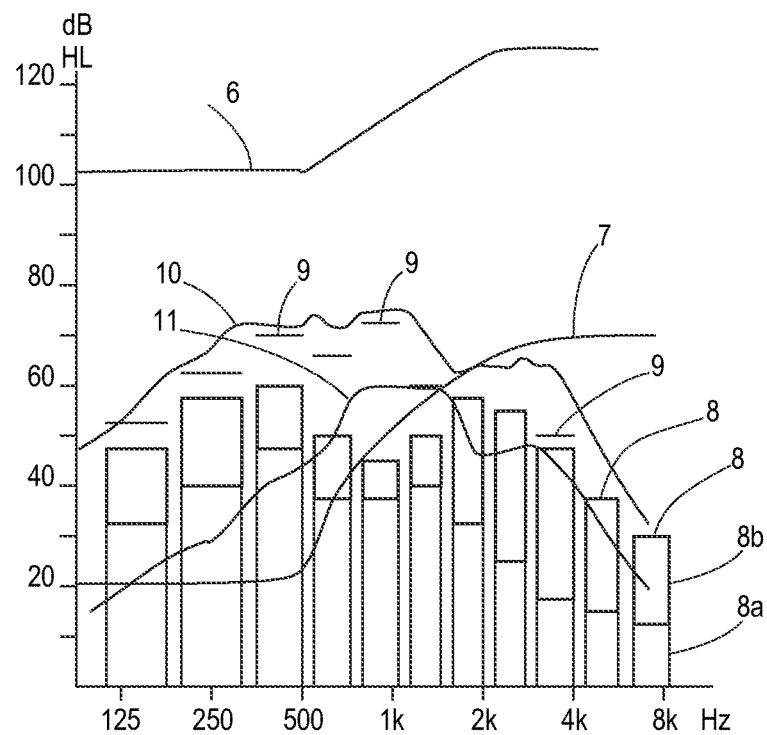
FIG. 2 illustrates the display of the results of the statistical analysis performed during the fitting.
Figure 3:
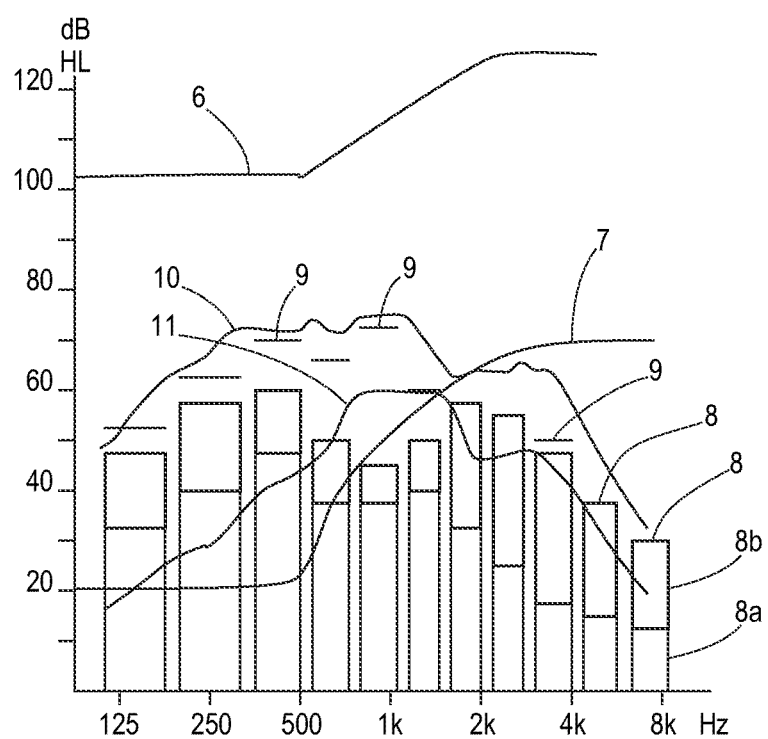
FIG. 3 illustrates an alternative display of the results of the statistical analysis performed during the fitting.

Often two hearing aids 2 are fitted at the same time, but for the sake of illustration one is thought to suffice. The hearing aid 2 is connected to an appropriate interface in the computer 1 via the cable 3, allowing signals to be communicated to and from the hearing aid 2 during the fitting procedure. The computer display 4, such as a screen, provides graphical information 5 about the hearing aid 2 to the fitter during the fitting procedure, as provided by fitting software running on the computer 2. FIGS. 2 and 3 are examples of such graphical information 5.

During a fitting session, the hearing aid is connected to the computer, the fitter operates the computer, and the intended hearing aid user wears the hearing aid. The fitter may launch various sub-sections of the fitting session, may enter program parameters into the hearing aid and may play sound samples to the user for providing him or her with an immediate impression of the acoustic performance of the hearing aid. The sound samples may be played by means of a loudspeaker or they may be played by the hearing aid itself through feeding an electric input signal via the cable connection 3 to the hearing aid, wherein the input signal is fed to the input side of the processor.

FIG. 2 illustrates a diagram with the frequency in hertz along the abscissa and output sound from the hearing aid in dB along the ordinate. Starting from the top the curve 6 illustrates the discomfort threshold for the user of the hearing aid 2. If this limit is exceeded by the sound output from the hearing aid 2 the user may sense discomfort or even pain. The curve 7 is the hearing threshold for the user of the hearing aid 2. If the sound output from the hearing aid 2 is below this threshold, the user cannot hear it. These curves are static and do not change during the fitting procedure.

The signal processing in modern digital hearing aids 2 is normally performed in a number of channels or frequency bands. In the example of FIG. 2, there is illustrated eleven such frequency bands, each represented by a column 8. Each column 8 represents the momentary sound output level from the hearing aid 2 in a given frequency band. This is a dynamic representation and the height of the columns change continually depending on the sound output level in each respective frequency band. Since these changes may be very rapid and the sound level very fluctuating, the input signal typically comprising a sequence of sounds, a number of peak markings 9 may designate the maximum sound levels for a short interval of time, i.e. a few seconds.

In order to provide more information about the current performance of the hearing aid 2, the columns 8 may be subdivided in visually distinguishable parts 8*a*, 8*b*. In FIG. 2 the lower, light gray part 8*a* represents the unprocessed input signal to the hearing aid 2. The upper darker gray part 8*b* represents the insertion gain added to the input signal by the hearing aid 2. Thus, the combined parts 8*a*, 8*b* for each column represent the output signal. During fitting, the fitter modifies the insertion gains represented by the columns 8*b* in each channel to adapt the hearing aid 2 to the actual hearing loss of the user. For different listening situations different schemes for the modification of the input signal may be devised.

As long as the input signal represented by columns 8*a* is a standardized signal, the fitter may still have a fairly good idea of what the hearing aid 2 does to the signal in addition to the amplification, irrespective of the fact that the signal is varying and irrespective of automated functions that may suddenly be activated by the hearing aid 2 itself.

This however may not be the case, when non-standardized sounds are used.

The inventor has discovered that performing a statistical analysis of the input signal, and displaying the results thereof may aid the fitter in understanding what the hearing aid 2 will do in terms of activation of automated functions.

Thus a statistical analysis is performed on the magnitude of the modified signal, i.e. the output signal. Preferably this is done in a number of frequency bands. The number of frequency bands need not be the same as the number of channels in the hearing aid 2, but could be far higher. The result of the statistical analysis is then presented to the fitter, e.g. in the form of curves 10, 11 representing upper and lower limits, respectively.

In the illustrated embodiment the statistical analysis is preformed by a percentile estimator, e.g. as disclosed in U.S. Pat. No. 5,687,241, the contents of which are incorporated herein by reference.

In one embodiment the statistical analysis is performed in the hearing aid 2 and the results are transmitted back to the computer 1 as parameters via the cable 3 for display on the display device 4. Transmission of parameters originating from the hearing aid is as such well known, and the skilled person will know to use an appropriate protocol such as the Digital Screwdriver (DSD) protocol developed by Etymotic Research Inc., which allows register values to be read from a hearing aid. Also, such transmission is disclosed in U.S. Pat. No. 4,989,251, the contents of which are incorporated herein by reference.

Preferably, the upper limit curve 10 represents the 90% percentile of the statistical analysis and the lower limit curve represents the 10% percentile. These percentile values are calculated continuously by the hearing aid 2 and the corresponding parameters are sent back to the computer 1 to update the curves 10 and 11 on the display.

However, if during the fitting the settings of the hearing aid 2 are modified, e.g. if the fitter changes the insertion gain in a frequency band, the statistical analysis is reset and new curves 10 and 11 displayed and updated. If not, data aggregated based on the old and no longer valid setting would influence the future statistical analysis and falsify the curves 10 and 11 displayed.

In another embodiment the statistical analysis is not performed in the hearing aid 2 but rather in the computer 1. In still another embodiment, the computer emulates the entire hearing aid, so that the presence of the actual hearing aid is not needed.

It should be noted that the statistical analysis might be performed in various different ways yielding different useful results. Thus, a statistical analysis based on fast Fourier transform or wavelets may be used. Also, to provide more information to the fitter, a three-dimensional graphic representation could be used, rather than two-dimensional graphic representation used in FIGS. 2 and 3.

FIG. 3 essentially differs from FIG. 2 on one point. For better visibility the area 12 between the two curves 10 and 11 has been filled in with color, thus making it easier to identify them among the other curves presented. In this respect, it should be noted that the FIGS. 2 and 3 are only examples and that at least some of the curves other than the curves 10 and 11 need not necessarily be shown.

Figure 4:
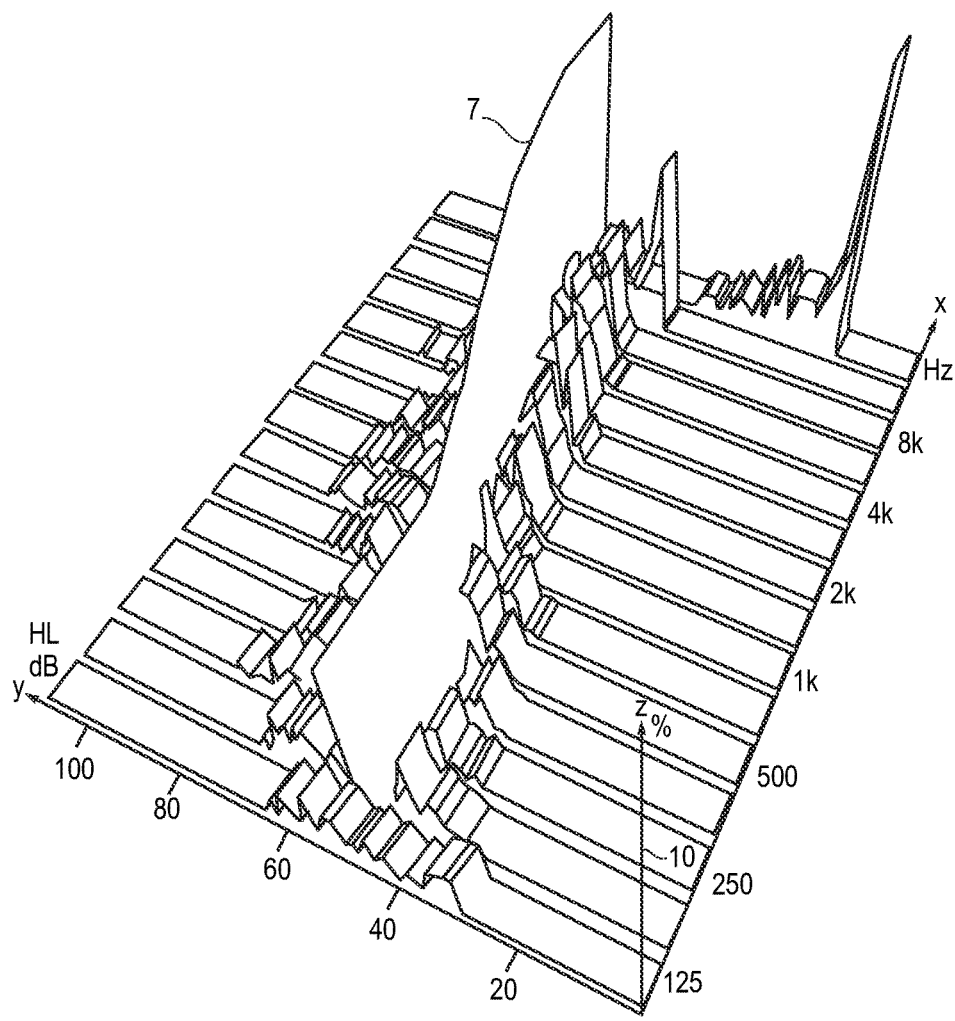
FIG. 4 illustrates a three-dimensional display of the statistical analysis according to the invention.

FIG. 4 shows a three-dimensional representation of the results of the statistical analysis, as performed in the hearing aid 2 or in a fitting computer 1 connected to the hearing aid 2 during the fitting. Like FIG. 2 and FIG. 3, FIG. 4 has the frequency along the x-axis (the abscissa) and the output level along the y-axis (the ordinate). However, further to these it has the statistical percentage along the z-axis (the third axis).

This then allows not only the representation of the curves corresponding to given percentiles as in FIG. 2 and FIG. 3, but also a representation of the actual distribution within these limits. Thus, for each frequency band, a plane parallel to the one spanned by the ordinate and the z-axis, represents a respective histogram of the statistical analysis. In other words, one could say that the area where the histograms raise above the plane spanned by the abscissa and the ordinate represents information similar to that in the curves represented in FIG. 2 and FIG. 3.

Figure 5:
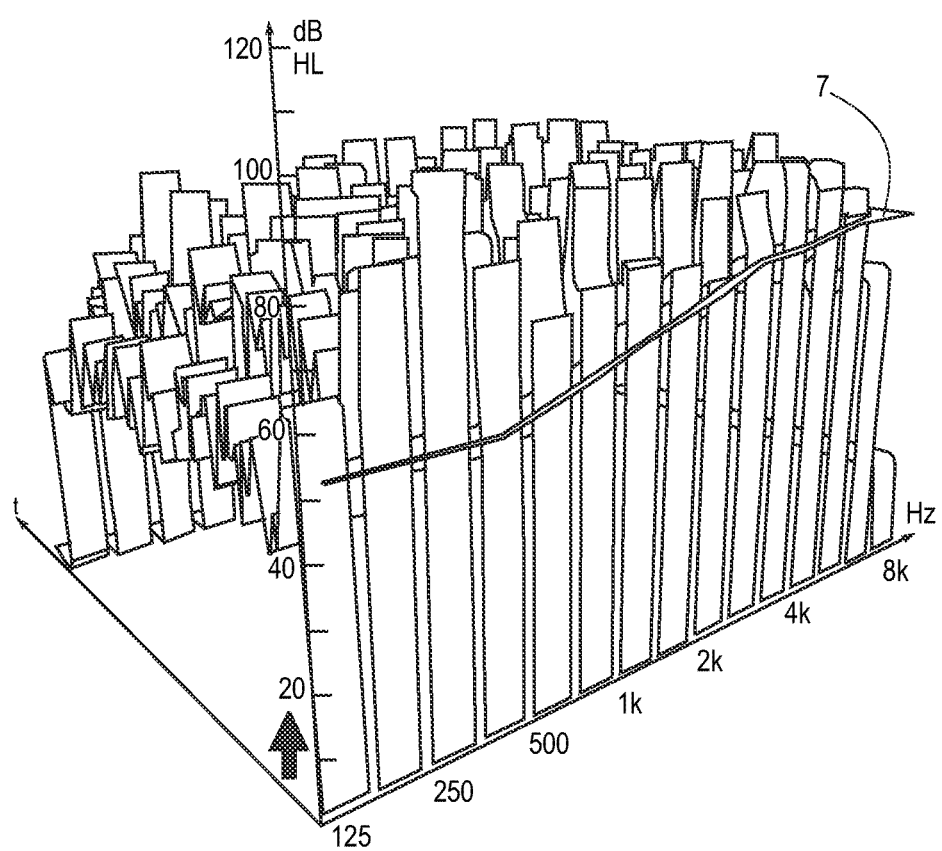
FIG. 5 illustrates a three-dimensional display showing the output level over time in each frequency band.

FIG. 5 shows the signal level over time for each frequency band. The frequency bands are again arranged along the abscissa, whereas time elapses along the ordinate. Along the third axis the signal level is displayed. The current signal level is always displayed in the plane spanned by the abscissa and the third axis, and historical signals recede backwards in the diagram along the ordinate.

This representation could be combined with that of FIG. 2 or FIG. 3, e.g. with the appropriate upper and lower limit statistical curves 10 and 11 displayed in the plane spanned by the abscissa and the third axis.

Moreover, this representation alone would give the fitter an impression of short term changes in the spectral distribution of the signals, so as to allow him to better assess what the hearing aid does in terms of automated functions relating to e.g. speech enhancement and noise suppression.

Figure 6:
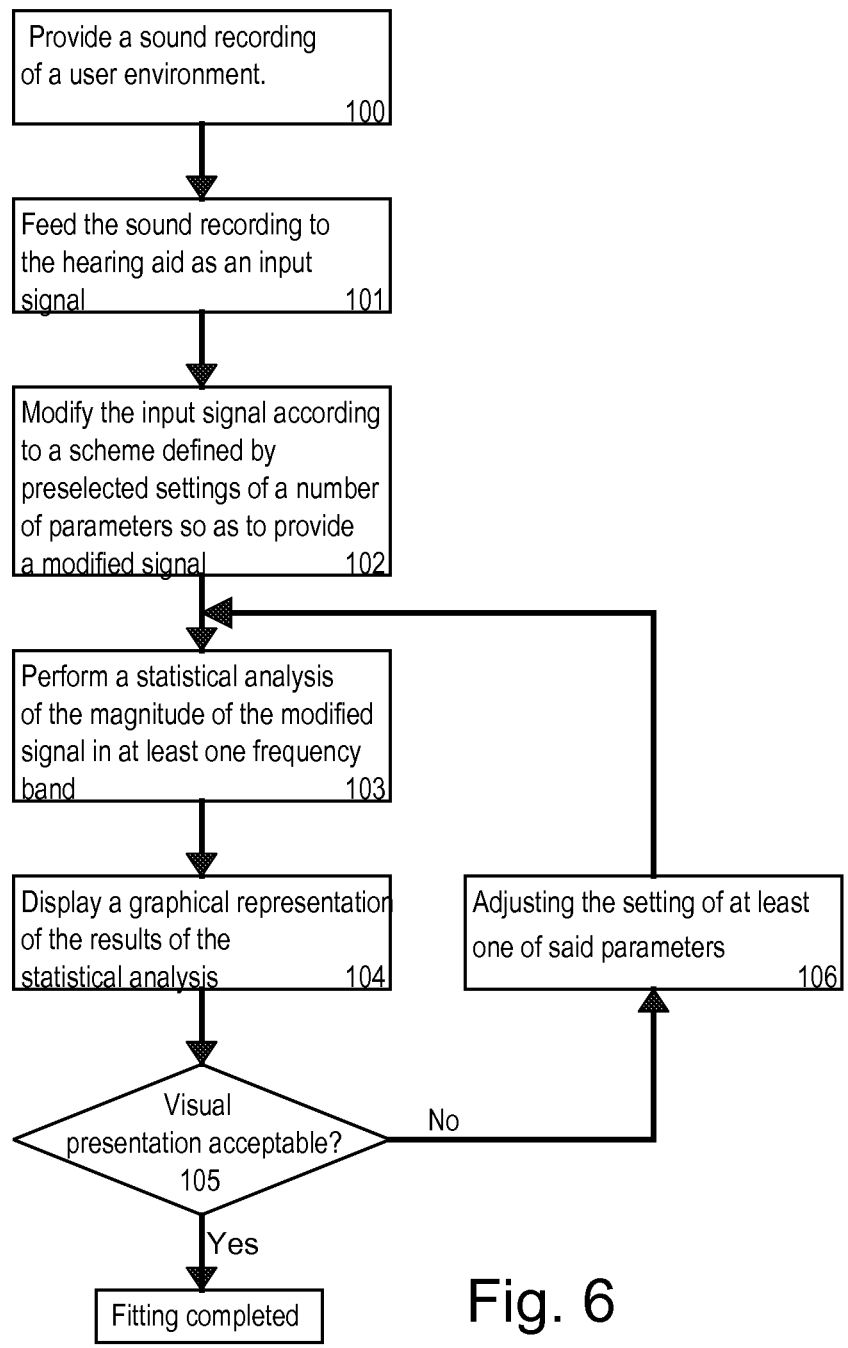
FIG. 6 illustrates the fitting process according to an embodiment of the present invention.

The fitting method according to one aspect of the invention will now be explained with reference to FIG. 6. In order to personalize the hearing aid to the actual user, and to the normal behavior of the user, a sound sample of a specific user's environment is recorded and provided to the fitting system 1, 2 at step 100. The sound recording is fed to the hearing aid 2 as an input signal at step 101. At step 102, the input signal is modified according to a scheme defined by preselected settings of a number of parameters so as to provide a modified signal. When starting the fitting process according to a preferred aspect of the invention, the values of the parameters are based upon measurements of the hearing loss HL of the user and standardized sound recordings. At step 103, a statistical analysis of the magnitude of the modified signal is performed in at least one frequency band. A graphical representation 5 of the results of the statistical analysis is displayed on the computer display 4 at step 104. At step 105, the fitter inspects the results of the statistical analysis visually, and based on his experience, he may deem the results as appropriate and the fitting process as completed. If the fitter is not yet satisfied with the result, he may then adjust the setting of one or more parameters at step 106. The computer will then restart the statistical analysis with the adjusted setting of the at least one of said parameters at step 106.

Though the above examples illustrate embodiments in which the statistical analysis is performed on the modified signal, i.e. the output signal, the skilled person will realize that the statistical analysis could just as well be performed directly on the input signal, e.g. if information on the input signal is more relevant to the fitter than the statistical information on the output signal.

Finally, the skilled person will appreciate that within the scope of the claims numerous modifications and adaptations of the method, system and hearing aid according to the invention, are possible. As an example the cable 3 could be substituted by a wireless connection.

The invention claimed is:

1. A method for fitting of a hearing aid to a hearing aid user by operating a fitting computer connected to the hearing aid during a fitting procedure, wherein the method comprises steps of:
    adjusting, via an operation interface of the fitting computer, a plurality of adjustable parameters in the hearing aid for providing compensation for a hearing loss of the hearing aid user, at least one of said parameters comprising an insertion gain;
    providing to said hearing aid an input signal representing one of a plurality sound recordings stored in the fitting computer, with said hearing aid providing a modified signal compensated for the hearing loss of the user;
    performing continuously, in the fitting computer, a statistical analysis of the magnitude of the modified signal while said user is wearing said hearing aid during the fitting procedure; and
    displaying, on the fitting computer while said hearing aid is producing sound based on said modified signal, and for a plurality of frequency bands, a graphical representation of the magnitude based on the statistical analysis together with an upper and lower magnitude limit based on the hearing loss of the hearing aid user for each of said plurality of frequency bands;
    adjusting the setting of at least one of said parameters based on the statistical analysis, and
    restarting the statistical analysis using the adjusted setting of the at least one of said parameters.

2. The method according to claim 1, wherein the displaying step further comprises displaying the magnitude of said input signal.

3. The method according to claim 1, wherein the statistical analysis is based on a percentile estimator, and where said upper and lower magnitude limits are based on respective upper and lower percentiles.

4. The method according to claim 1, wherein the upper percentile is a 90% percentile.

5. The method according to claim 3, wherein the lower percentile is a 10% percentile.

6. The method according to claim 1, wherein the upper and lower magnitude limits are displayed as continuous curves as respective functions of frequency.

7. The method according to claim 1, wherein said statistical analysis is performed using a fast Fourier transform.

8. The method according to claim 1, wherein the fitting of said hearing aid is provided as a remote fitting session and the connection between the fitting computer and the hearing aid is provided as a wireless connection.

9. A fitting computer for fitting of a hearing aid to a hearing aid user while said computer is connected to said hearing aid during a fitting procedure, wherein said fitting computer comprises:
    an operation interface for adjusting a plurality of adjustable parameters in the hearing aid so that said hearing aid will provide a modified signal compensated for a hearing loss of the hearing aid user, at least one of said parameters comprising an insertion gain, and said operation interface allowing the fitter to play one of a plurality sound recordings stored in the fitting computer for the hearing aid user when wearing said hearing aid;
    a statistical analysis component configured to continuously perform a statistical analysis of the magnitude of said modified signal while one of said plurality sound recordings is played for the hearing aid user wearing said hearing aid during the fitting procedure; and a display for displaying, for a plurality of frequency bands, a graphical representation of the magnitude based on the statistical analysis while playing said one of said plurality sound recordings played for the hearing aid user wearing said hearing aid, said graphical representation including display of an upper and lower magnitude limit based on the hearing loss of the hearing aid user for each of said plurality of frequency bands;

wherein said operation interface allows adjustment of at least said insertion gain based on said statistical analysis, and said statistical analysis component is configured to restart the statistical analysis using the adjusted setting of the insertion gain.

10. The fitting computer according to claim 9, wherein the magnitude of said modified signal is displayed together with the magnitude of a signal fed to the hearing aid representing the played one of said sound recordings.

11. The fitting computer according to claim 9, comprising a percentile estimator calculating said upper and lower magnitude limits based on respective upper and lower percentiles.

12. The fitting computer according to claim 11, wherein the percentile estimator calculates the upper magnitude limit as a 90% percentile.

13. The fitting computer according to claim 11, wherein the percentile estimator calculates the lower magnitude limit as a 10% percentile.

14. The fitting computer according to claim 9, wherein said display displays the upper and lower magnitude limits as continuous curves as respective functions of frequency.

15. The fitting computer according to claim 9, wherein said statistical analysis component performs said statistical analysis using a fast Fourier transform.

16. The fitting computer according to claim 9, wherein the connection between the fitting computer and the hearing aid is provided as a wireless connection for remote fitting.

17. A non-transitory computer-readable storage medium having stored thereon non-transient computer-readable instructions which, when executed on a fitting computer connected to a hearing aid during fitting, will cause the following method to be performed:

providing an operation interface for a fitter fitting the hearing aid;

offering, via said operation interface, and a plurality sound recordings representing sound environments important to the hearing aid user;

allowing the fitter, via the operation interface, to adjust a plurality of adjustable parameters of said hearing aid whereby said hearing aid will provide a modified signal compensated for a hearing loss of the hearing aid user, at least one of said parameters comprising an insertion gain;

allowing the fitter, via the operation interface, to play one of said plurality sound recordings for the hearing aid user when wearing said hearing aid;

performing a statistical analysis of the magnitude of said modified signal while said user is wearing said hearing aid during the fitting; and displaying for a plurality of frequency bands a graphical representation of the magnitude based on the statistical analysis while playing said one of said plurality sound recordings played for the hearing aid user wearing said hearing aid, said graphical representation including a display of an upper and lower magnitude limit based on the hearing loss of the hearing aid user for each of said frequency bands;

wherein, following adjustment of at least said insertion gain based on said statistical analysis, said statistical analysis is restarted using an adjusted setting of the insertion gain.

18. A method for the fitting of a hearing aid to a specific user by operating a fitting computer in communication with said hearing aid during a fitting procedure, said method comprising the steps of providing to said hearing aid from said fitting computer an input signal representing a sound recording of a specific user environment, said specific user environment comprising at least one location in which said user will use said hearing aid, modifying the input signal at said hearing aid according to a scheme defined by preselected settings of a number of parameters so as to compensate for a hearing loss of said user, to provide a modified signal, at least one of said parameters comprising an insertion gain, performing continuously, in the fitting computer and during said fitting procedure, a statistical analysis of the magnitude of at least one of the modified signal and the input signal in at least one frequency band, displaying, on the fitting computer and for a plurality of frequency bands, a graphical representation of said magnitude based on the results of the statistical analysis, together with an upper and lower magnitude limit based on the hearing loss of the hearing aid user for each of said plurality of frequency bands, adjusting the setting of at least said insertion gain based on said statistical analysis, and restarting the statistical analysis using the adjusted setting of said insertion gain.

* * * * *